(12) United States Patent
Bhat et al.

(10) Patent No.: US 10,016,529 B2
(45) Date of Patent: *Jul. 10, 2018

(54) BIOMATERIAL COMPOSITIONS, IMPLANTS, AND METHODS OF MAKING THE SAME

(71) Applicant: GLOBUS MEDICAL, INC., Audubon, PA (US)

(72) Inventors: Archana Bhat, Phoenixville, PA (US); Vipin Kunjachan, Audubon, PA (US); Chris Geisler, Philadelphia, PA (US); Allison Adams, Philadelphia, PA (US); Christine Grimes, Jeffersonville, PA (US)

(73) Assignee: Globus Medical, Inc., Audubon, PA (US)

( * ) Notice: Subject to any disclaimer, the term of this patent is extended or adjusted under 35 U.S.C. 154(b) by 247 days.

This patent is subject to a terminal disclaimer.

(21) Appl. No.: 14/735,460

(22) Filed: Jun. 10, 2015

(65) Prior Publication Data

US 2016/0361461 A1 Dec. 15, 2016

(51) Int. Cl.
*A61L 27/44* (2006.01)
*A61L 27/46* (2006.01)
*A61L 27/56* (2006.01)

(52) U.S. Cl.
CPC ............. *A61L 27/446* (2013.01); *A61L 27/46* (2013.01); *A61L 27/56* (2013.01); *A61L 2430/02* (2013.01); *A61L 2430/38* (2013.01)

(58) Field of Classification Search
CPC .... A61L 27/446; A61L 27/46; A61L 2430/02; C08L 5/08; C08L 71/02
USPC .................................................. 514/967, 51
See application file for complete search history.

(56) References Cited

U.S. PATENT DOCUMENTS

| | | | |
|---|---|---|---|
| 4,437,191 A | 3/1984 | van der Zel et al. |
| 5,681,872 A | 10/1997 | Erbe |
| 5,700,289 A | 12/1997 | Breitbart et al. |
| 5,776,193 A | 7/1998 | Kwan et al. |
| 5,854,207 A | 12/1998 | Lee et al. |
| 5,899,939 A | 5/1999 | Boyce et al. |
| 5,914,356 A | 6/1999 | Erbe |
| 5,939,039 A | 8/1999 | Sapieszko et al. |
| 6,123,731 A | 9/2000 | Boyce et al. |
| 6,264,701 B1 | 7/2001 | Brekke |
| 6,294,041 B1 | 9/2001 | Boyce et al. |
| 6,309,659 B1 | 10/2001 | Clokie |
| 6,350,283 B1 | 2/2002 | Michelson |
| 6,372,257 B1 | 4/2002 | Marchosky |
| 6,432,436 B1 | 8/2002 | Gertzman et al. |
| 6,437,018 B1 | 8/2002 | Gertzman et al. |
| 6,666,890 B2 | 12/2003 | Michelson |
| 6,696,073 B2 | 2/2004 | Boyce et al. |
| 6,706,067 B2 | 3/2004 | Shimp et al. |
| 6,723,131 B2 | 4/2004 | Muschler |
| 6,749,636 B2 | 6/2004 | Michelson |
| 6,752,831 B2 | 6/2004 | Sybert et al. |
| 6,776,800 B2 * | 8/2004 | Boyer, II ........... A61B 17/0401 623/16.11 |
| 6,808,585 B2 | 10/2004 | Boyce et al. |
| 6,843,807 B1 | 1/2005 | Boyce et al. |
| 6,919,308 B2 | 7/2005 | Oppermann et al. |
| 6,949,251 B2 | 9/2005 | Dalal et al. |
| 7,022,137 B2 | 4/2006 | Michelson |
| 7,041,641 B2 | 5/2006 | Rueger et al. |
| 7,132,110 B2 | 11/2006 | Kay et al. |
| 7,156,880 B2 | 1/2007 | Evans et al. |
| 7,168,133 B2 | 1/2007 | Luo et al. |
| 7,175,858 B2 | 2/2007 | Constantz et al. |
| 7,235,107 B2 | 6/2007 | Evans et al. |
| 7,262,003 B2 | 8/2007 | Kumar et al. |
| 7,275,933 B2 | 10/2007 | Jia et al. |
| 7,291,345 B2 | 11/2007 | Winterbottom et al. |
| 7,332,452 B2 | 2/2008 | Ogawa et al. |
| 7,390,498 B2 | 6/2008 | Dalal et al. |
| 7,393,405 B2 | 7/2008 | Bohner |
| 7,473,678 B2 | 1/2009 | Lynch |
| 7,494,950 B2 | 2/2009 | Armitage et al. |
| 7,498,041 B2 | 3/2009 | Masinaei et al. |
| 7,517,489 B2 | 4/2009 | Akash |
| 7,582,309 B2 | 9/2009 | Rosenberg et al. |
| 7,611,536 B2 | 11/2009 | Michelson |
| 7,723,395 B2 | 5/2010 | Ringeisen |
| 7,744,597 B2 | 6/2010 | Gaskins et al. |
| 7,776,100 B2 | 8/2010 | Brekke et al. |
| 7,785,634 B2 | 8/2010 | Borden |
| 7,811,608 B2 | 10/2010 | Kay et al. |
| 7,824,702 B2 | 11/2010 | Wironen et al. |
| 7,833,278 B2 | 11/2010 | Evans et al. |
| 7,887,598 B2 | 2/2011 | Evans et al. |
| 7,892,291 B2 | 2/2011 | Evans et al. |
| 7,910,690 B2 | 3/2011 | Ringeisen et al. |
| 7,931,692 B2 | 4/2011 | Sybert et al. |
| 7,939,108 B2 | 5/2011 | Morris et al. |
| 7,942,961 B2 | 5/2011 | Asgarg |
| 7,947,759 B2 | 5/2011 | Lin et al. |
| 7,959,941 B2 | 6/2011 | Knaack et al. |
| 7,977,094 B2 | 7/2011 | Masinaei et al. |
| 8,002,813 B2 | 8/2011 | Scarborough et al. |
| 8,067,078 B1 | 11/2011 | Espinosa et al. |

(Continued)

FOREIGN PATENT DOCUMENTS

| | | | |
|---|---|---|---|
| CA | 1341610 C | 4/1989 | |
| CA | 2027259 C | 12/2000 | |
| WO | 2005084701 A1 | 9/2005 | |
| WO | WO-2013036568 A1 * | 3/2013 | ............... A61K 8/65 |
| WO | 2014128289 A1 | 8/2014 | |

OTHER PUBLICATIONS

Humana, Bone Graft Substitutes, Feb. 23, 2012 p. 1-21.*

(Continued)

*Primary Examiner* — Michael G Hartley
*Assistant Examiner* — Nabila G Ebrahim

(57) ABSTRACT

Biomaterials, implants made therefrom, methods of making the biomaterial and implants, methods of promoting bone or wound healing in a mammal by administering the biomaterial or implant to the mammal, and kits that include such biomaterials, implants, or components thereof. The biomaterials may be designed to exhibit osteogenic, osteoinductive, osteoconductive, and/or osteostimulative properties.

18 Claims, No Drawings

(56) References Cited

U.S. PATENT DOCUMENTS

| | | |
|---|---|---|
| 8,093,313 B2 | 1/2012 | Miller |
| 8,105,383 B2 | 1/2012 | Michelson |
| 8,137,403 B2 | 3/2012 | Michelson |
| 8,147,860 B2 | 4/2012 | Rosenberg et al. |
| 8,147,862 B2 | 4/2012 | McKay |
| 8,163,032 B2 | 4/2012 | Evans et al. |
| 8,188,229 B2 | 5/2012 | Ringeison et al. |
| 8,197,474 B2 | 6/2012 | Scarborough et al. |
| 8,202,539 B2 | 6/2012 | Behnam et al. |
| 8,221,781 B2 | 7/2012 | Rosenberg et al. |
| 8,232,327 B2 | 7/2012 | Garigapati et al. |
| 8,268,008 B2 | 9/2012 | Betz et al. |
| 8,287,915 B2 | 10/2012 | Clineff et al. |
| 8,303,967 B2 | 11/2012 | Clineff et al. |
| 8,303,971 B2 | 11/2012 | Cieslik et al. |
| 8,309,106 B2 | 11/2012 | Masinaei et al. |
| 8,323,700 B2 | 12/2012 | Morris et al. |
| 8,328,876 B2 | 12/2012 | Behnam et al. |
| 8,333,985 B2 | 12/2012 | Knaack et al. |
| 8,357,384 B2 | 1/2013 | Behnam et al. |
| 8,394,141 B2 | 3/2013 | Mills et al. |
| 8,399,409 B2 | 3/2013 | Lynch et al. |
| 8,419,802 B2 | 4/2013 | Evans et al. |
| 8,425,619 B2 | 4/2013 | Evans et al. |
| 8,435,306 B2 | 5/2013 | Evans et al. |
| 8,435,343 B2 | 5/2013 | Yahav et al. |
| 8,435,566 B2 | 5/2013 | Behnam et al. |
| 8,454,988 B2 | 6/2013 | Rosenberg et al. |
| 8,460,686 B2 | 6/2013 | Clineff et al. |
| 8,475,824 B2 | 7/2013 | McKay |
| 8,506,981 B1 | 8/2013 | Borden |
| 8,506,985 B2 | 8/2013 | Garcia De Castro Andrews et al. |
| 8,524,265 B2 | 9/2013 | McKay |
| 8,529,962 B2 | 9/2013 | Morris et al. |
| 8,545,858 B2 | 10/2013 | Rosenberg et al. |
| 8,545,864 B2 | 10/2013 | Morris et al. |
| 8,551,519 B2 | 10/2013 | Bezwada |
| 8,551,525 B2 | 10/2013 | Cook et al. |
| 8,562,648 B2 | 10/2013 | Kaes et al. |
| 8,580,865 B2 | 11/2013 | Peters et al. |
| 8,597,675 B2 | 12/2013 | Murphy et al. |
| 8,613,938 B2 | 12/2013 | Akella et al. |
| 8,623,094 B2 | 1/2014 | Evans et al. |
| 8,641,774 B2 | 2/2014 | Rahaman et al. |
| 8,642,061 B2 | 2/2014 | Shimp et al. |
| 8,652,503 B2 | 2/2014 | Wironen et al. |
| 8,663,326 B2 | 3/2014 | Osman |
| 8,663,672 B2 | 3/2014 | Manrique et al. |
| 8,663,677 B2 | 3/2014 | Fu et al. |
| 8,685,429 B2 | 4/2014 | Koblish et al. |
| 8,734,525 B2 | 5/2014 | Behnam et al. |
| 8,740,987 B2 | 6/2014 | Geremakis et al. |
| 8,747,899 B2 | 6/2014 | Chaput et al. |
| 8,753,391 B2 | 6/2014 | Lu et al. |
| 8,753,689 B2 | 6/2014 | Morris et al. |
| 8,758,792 B2 | 6/2014 | Behnam et al. |
| 8,778,378 B2 | 7/2014 | Clineff et al. |
| 8,795,382 B2 | 8/2014 | Lin et al. |
| 8,802,626 B2 | 8/2014 | Rueger et al. |
| 8,834,928 B1 | 9/2014 | Truncale et al. |
| 8,864,843 B2 | 10/2014 | Lu et al. |
| 8,871,235 B2 | 10/2014 | Borden |
| 8,876,532 B2 | 11/2014 | Atkinson et al. |
| 8,877,221 B2 | 11/2014 | McKay |
| 8,883,210 B1 | 11/2014 | Truncale et al. |
| 8,926,710 B2 | 1/2015 | McKay |
| 8,992,964 B2 | 3/2015 | Shelby et al. |
| 8,992,965 B2 | 3/2015 | Behnam |
| 2001/0018614 A1* | 8/2001 | Bianchi ............... A61F 2/28 623/16.11 |
| 2001/0038848 A1 | 11/2001 | Donde et al. |
| 2002/0076429 A1 | 6/2002 | Wironen et al. |
| 2002/0098222 A1 | 7/2002 | Wironen et al. |
| 2002/0193883 A1 | 12/2002 | Wironen |
| 2003/0009235 A1 | 1/2003 | Manrique et al. |
| 2003/0055512 A1 | 3/2003 | Genin et al. |
| 2003/0149437 A1 | 8/2003 | Livne et al. |
| 2004/0075192 A1 | 4/2004 | Boyer, II et al. |
| 2004/0091462 A1 | 5/2004 | Lin et al. |
| 2004/0243242 A1 | 12/2004 | Sybert et al. |
| 2005/0118230 A1 | 6/2005 | Hill et al. |
| 2005/0251267 A1 | 11/2005 | Winterbottom et al. |
| 2005/0281856 A1 | 12/2005 | McGlohorn et al. |
| 2006/0018942 A1 | 1/2006 | Rowe et al. |
| 2006/0036331 A1 | 2/2006 | Lu et al. |
| 2006/0147545 A1 | 7/2006 | Scarborough et al. |
| 2007/0083270 A1 | 4/2007 | Masinaei et al. |
| 2007/0098756 A1 | 5/2007 | Behnam |
| 2007/0105222 A1 | 5/2007 | Wolfinbarger et al. |
| 2007/0113951 A1 | 5/2007 | Huang |
| 2008/0033572 A1 | 2/2008 | D'Antonio et al. |
| 2008/0069852 A1 | 3/2008 | Shimp et al. |
| 2008/0091270 A1 | 4/2008 | Miller et al. |
| 2008/0187571 A1 | 8/2008 | Clineff et al. |
| 2008/0234822 A1 | 9/2008 | Govil |
| 2009/0012625 A1 | 1/2009 | Ying et al. |
| 2009/0074753 A1 | 3/2009 | Lynch |
| 2009/0157087 A1 | 6/2009 | Wei et al. |
| 2009/0192474 A1 | 7/2009 | Wei et al. |
| 2009/0312842 A1 | 12/2009 | Bursac et al. |
| 2009/0317447 A1 | 12/2009 | Hsiao et al. |
| 2010/0055078 A1 | 3/2010 | Hughes-Fulford |
| 2010/0145469 A1 | 6/2010 | Barralet et al. |
| 2010/0196333 A1 | 8/2010 | Gaskins et al. |
| 2010/0203155 A1 | 8/2010 | Wei et al. |
| 2010/0234966 A1 | 9/2010 | Lo |
| 2011/0045044 A1 | 2/2011 | Masinaei et al. |
| 2011/0066242 A1 | 3/2011 | Lu et al. |
| 2011/0070312 A1 | 3/2011 | Wei et al. |
| 2011/0117018 A1 | 5/2011 | Hart et al. |
| 2011/0117165 A1 | 5/2011 | Melican et al. |
| 2011/0117166 A1 | 5/2011 | Melican |
| 2011/0117171 A1 | 5/2011 | Melican et al. |
| 2011/0144764 A1 | 6/2011 | Bagga et al. |
| 2011/0224675 A1 | 9/2011 | Tofighi et al. |
| 2011/0262554 A1 | 10/2011 | Masinaei et al. |
| 2011/0276147 A1 | 11/2011 | Cook et al. |
| 2011/0280924 A1 | 11/2011 | Lin et al. |
| 2012/0053692 A1 | 3/2012 | Voor et al. |
| 2012/0064290 A1 | 3/2012 | Esat et al. |
| 2012/0093895 A1 | 4/2012 | Song et al. |
| 2012/0164187 A1 | 6/2012 | Ollila et al. |
| 2012/0237568 A1 | 9/2012 | Murphy et al. |
| 2013/0013071 A1 | 1/2013 | Betz et al. |
| 2013/0059011 A1* | 3/2013 | Clineff ............... A61L 27/10 424/602 |
| 2013/0059382 A1 | 3/2013 | Tsai et al. |
| 2013/0122057 A1 | 5/2013 | Garigapati et al. |
| 2013/0144376 A1 | 6/2013 | Dave et al. |
| 2013/0145963 A1 | 6/2013 | Cai et al. |
| 2013/0150227 A1 | 6/2013 | Wang et al. |
| 2013/0189338 A1 | 7/2013 | Drapeau et al. |
| 2013/0195805 A1 | 8/2013 | Wei et al. |
| 2013/0202670 A1 | 8/2013 | Darmac et al. |
| 2013/0236513 A1 | 9/2013 | Guelcher et al. |
| 2013/0244942 A1 | 9/2013 | Benedict et al. |
| 2013/0274890 A1 | 10/2013 | McKay |
| 2013/0282138 A1 | 10/2013 | McKay |
| 2013/0297038 A1 | 11/2013 | McKay |
| 2014/0031950 A1 | 1/2014 | Cook et al. |
| 2014/0079753 A1 | 3/2014 | Darby et al. |
| 2014/0079789 A1* | 3/2014 | Pomrink ........... A61K 47/48992 424/493 |
| 2014/0170202 A1 | 6/2014 | Peters et al. |
| 2014/0195005 A1 | 7/2014 | McKay |
| 2014/0205674 A1 | 7/2014 | Wei |
| 2014/0212471 A1 | 7/2014 | Drapeau et al. |
| 2014/0222159 A1 | 8/2014 | Bursac et al. |
| 2014/0271779 A1 | 9/2014 | Bagga et al. |
| 2014/0271786 A1 | 9/2014 | Bagga et al. |
| 2014/0271914 A1 | 9/2014 | Wagner |
| 2014/0294913 A1 | 10/2014 | Hasirci et al. |

(56) References Cited

U.S. PATENT DOCUMENTS

2014/0314822 A1 10/2014 Carter et al.
2015/0010607 A1 1/2015 Francis et al.
2015/0223937 A1* 8/2015 Ortiz ........................ A61L 27/46
623/23.61

OTHER PUBLICATIONS

Coathup et al., The effect of particle size on the osteointegration of injectable silicate-substituted calcium phosphate bone substitute materials, Biomed Mater Res Part B 2013:101B:902-910.*
Hesse et al., Collagen type I hydrogel allows migration, proliferation and osteogenic differentiation of rat bone marrow stromal cells, J Biomed Mater Res A. Aug. 2010; 94(2): 442-449.*

* cited by examiner

BIOMATERIAL COMPOSITIONS, IMPLANTS, AND METHODS OF MAKING THE SAME

TECHNICAL FIELD

The present invention relates generally to bone and wound healing biomaterials. The invention relates to the biomaterials and implants formed therefrom. The invention also relates to methods of making the materials and implants, and methods of promoting bone or wound healing in a mammal by administering the biomaterial or implant to the mammal. The invention further relates to kits that include one or more of the biomaterials, implants, or components thereof.

BACKGROUND

Bone grafting is a surgical procedure that replaces missing bone and/or repairs bone fractures. Bone generally has the ability to regenerate well but may require a scaffold to do so. Bone grafts may be allograft (cadaveric bone e.g., from a bone bank), autologous (i.e., bone harvested from the patient's own body, for example from the iliac crest), or synthetic. Most bone grafts are expected to be resorbed and replaced as the natural bone heals over time.

Successful biomaterials may include osteoconduction (guiding the reparative growth of the natural bone), osteoinduction (encouraging undifferentiated cells to become active osteoblasts), and/or osteogenesis (living bone cells in the graft material contributing to bone remodeling). Although traditional bone grafts may exhibit certain advantages, traditional allograft may not exhibit the properties desired, may be difficult to obtain, or may not be in a shape or form suitable for implantation.

SUMMARY

To meet this and other needs, biomaterials described herein may be osteogenic, osteoinductive, osteoconductive, and/or osteostimulative, which may be advantageous for bone healing and repair and without the drawbacks of present allograft or autograft products. The biomaterial compositions or implants prepared therefrom can include various combinations of demineralized bone matrix (e.g., in the form of chips, fibers, or particulates), ceramics such as tricalcium phosphate, bioactive glass, and combinations thereof, a carrier such as a carrier composition containing hyaluronic acid and/or collagen, and one or more additional components each of which is described in more detail herein.

According to one embodiment, a method of making a biomaterial composition for aiding bone regeneration includes mixing a carrier with a ceramic composition including bioactive glass and calcium phosphate (e.g., beta-tricalcium phosphate) to form a biomaterial composition; adding the biomaterial composition to a mold to form a molded biomaterial composition; freeze-drying the molded biomaterial composition to form a freeze-dried composition; and crosslinking the freeze-dried composition to form a crosslinked composition. In addition, demineralized bone matrix (e.g., in the form of cortical fibers, bone chips, particulates, or the like) may be added to the biomaterial composition during the mixing step. Optionally, the method may further include crosslinking the freeze-dried composition with a chemical crosslinking agent (e.g., formaldehyde). Optionally, the method may further include sterilizing the composition, for example, with ethylene oxide and/or gamma radiation.

The biomaterial composition may also include one or more of the following attributes. The carrier may include one or more of hyaluronic acid, poloxamer, glycerol, polyethylene glycol, or the like. If hyaluronic acid is used as the carrier, for example, the hyaluronic acid may be swellable to gel form. For example, the hyaluronic acid may be mixed with water or an acid, such as hydrochloric acid, which causes the carrier to swell in volume. The bioactive glass may have a bimodal or unimodal particle size distribution. The particle size may range, for example, from about 1 to 1000 μm. The final form of the biomaterial composition may be the material itself or an implant formed therefrom. The composition or implant may be a strip, gel, putty, sponge, or the like.

According to another embodiment, a method of promoting bone or wound healing in a mammal includes providing a biomaterial composition comprising a carrier and a ceramic composition including bioactive glass and calcium phosphate (e.g., the biomaterial composition may include about 5-20% (w/w) of the carrier, about 15-20% (w/w) of the bioactive glass, and about 60-70% (w/w) of the calcium phosphate); and administering the biomaterial composition into a target repair site to facilitate repair or regeneration of bone at the target repair site. For example, the target repair site may include an injury or defect in the spine (e.g., in the cervical, thoracic, or lumbar regions).

According to another embodiment, a biomaterial composition or implant derived therefrom includes one or more of: one or more carriers, one or more ceramics, one or more demineralized bone products, and combinations thereof. By way of non-limiting example, the carrier may include a carrier composition containing hyaluronic acid and/or collagen; the ceramics may include tricalcium phosphate, bioactive glass, and combinations thereof; and the demineralized bone products may be in the form of chips, fibers, or particulates, for example, derived from cortical bone, cancellous bone, or a combination of both. The implant may be shaped, for example, in the form of a strip, ring, cylinder, plug, or the like. The implant may be used alone or in combination with a cage, frame, allograft, graft material, or other biomaterials known in the art.

According to yet another embodiment, a kit includes one or more biomaterials, implants, or components thereof described herein. For example, the kit may contain putty, gel, strip, and/or extrudable versions of the biomaterial compositions. The kit may contain biomaterial compositions of the same or different types. In addition, the kit may include other components known in the art, including, but not limited to, carriers or scaffolds, cages (e.g., titanium and/or polyether ether ketone (PEEK) spacers), allograft spacers, cell culture media, phosphate buffered saline (PBS), a tissue culture substrate, bone graft harvesting tools, bone marrow aspirate retrieval tools, or the like.

DETAILED DESCRIPTION

The present invention relates generally to biomaterials and implants made therefrom that may exhibit osteogenic, osteoinductive, osteoconductive, and/or osteostimulative properties. The invention also relates to methods of making the biomaterial and implants, and methods of promoting bone or wound healing in a mammal by administering the biomaterial or implant to the mammal. The invention further relates to kits that include one or more of the biomaterials, implants, or components thereof.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments of modifications thereof are contemplated as falling within the scope of this disclosure and equivalents thereto.

In describing example embodiments, specific terminology is employed for the sake of clarity. However, the embodiments are not intended to be limited to this specific terminology. Unless otherwise noted, technical terms are used according to conventional usage.

As used herein, "a" or "an" may mean one or more. As used herein "another" may mean at least a second or more. As used herein, unless otherwise required by context, singular terms include pluralities and plural terms include the singular.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of."

Unless specified otherwise, all values provided herein include up to and including the endpoints given, and the values of the constituents or components of the compositions are expressed in weight percent or % by weight of each ingredient in the composition.

Each compound used herein may be discussed interchangeably with respect to its chemical formula, chemical name, abbreviation, etc. For example, PEG may be used interchangeably with polyethylene glycol.

Embodiment described herein may be generally directed to biomaterials, implants made therefrom, methods of making the same, and methods of using the same to promote healing or fusion of bone. Although biomaterials or implants may be discussed separately, it will be appreciated by one of ordinary skill in the art that the biomaterials described may be used in and of itself or may be used to create implants of different shapes, sizes, and orientations for a number of different clinical outcomes. Thus, the discussion of biomaterials may apply equally to the discussion on implants and vice versa.

The biomaterial composition may be osteogenic, osteoinductive, osteoconductive, and/or osteostimulative, which may be advantageous for bone healing and repair. The biomaterials may be osteoconductive when the material serves as a scaffold that provides surface area for new bone growth. The biomaterials may be osteoinductive if they stimulate osteoprogenitor cells or induce mesenchymal stem cells to differentiate into osteoblasts that then begin new bone formation. Biomaterials may be osteogenic if they contain cells (e.g., viable cells) that are capable of bone regeneration. The biomaterial may be osteostimulative if the material accelerates the bone formation process. The composition may also be "biocompatible" as that term refers to the ability (e.g., of a composition or material) to perform with an appropriate host response in a specific application, or at least to perform without having a toxic or otherwise deleterious effect on a biological system of the host, locally or systemically. The biomaterial and/or implant may be "biologically degradable" in that the material may be degraded by cellular absorption and/or hydrolytic degradation in a patient's body. According to some embodiments, it may be desirable that the biomaterials possess sufficient osteoconductivity, porosity, mechanical strength, and degradation times. For example, the composition may be biologically degradable over a period of time of about 3-12 months, about 3-9 months, about 3-6 months, about 6-12 months, about 6-9 months, or about 9-12 months.

According to one embodiment, the biomaterial composition may be configured to facilitate repair or regeneration of bone at a target repair site. The target repair site can be, for example, a void, gap, or other defect or surgeon created opening in a bone, between bones, or other bony structure in a body of a patient. For example, the biomaterial composition can be configured to facilitate bone growth at a target repair site in the spine, pelvis, an extremity, the cranium, or another bone, between bones, or bony structure in the patient's body. The biomaterial composition may be configured to be directly implanted or otherwise disposed at and in contact with the target repair site.

The biomaterial composition can include various combinations of demineralized bone matrix (e.g., in the form of chips, fibers, or particulates), ceramic such as calcium phosphate or bioactive glass, collagen, and one or more additional components each of which is described in more detail herein.

According to certain embodiments, the compositions may include demineralized bone matrix. Demineralized bone matrix (also known as DBM) may provide osteoconductive, osteoinductive and/or osteogenic properties. Thus, it induces the formation of bone tissue. As used herein, the terms "demineralized bone", "demineralized bone matrix", and "DBM" may be used interchangeably. The demineralized bone, for example, in the form of fibers, chips, and/or particles, can be disposed on, embedded within, and or mixed within the biomaterial composition.

Demineralized bone matrix may be in the form of sheets, fibers, threads, strips, chips, shards, elongated particles, powder, or particulates, for example. The demineralized bone matrix may include bone pieces of all shapes, sizes, thickness, and configurations that possess regular, irregular, or random geometries. For example, fibers may have an average fiber length of about 250 µm to about 2 mm, about 250 micrometers to about 750 micrometers, about 750 micrometers to about 1.25 millimeters, or about 1.25 millimeters to about 2 millimeters. In addition, the fibers may have an aspect ratio (defined as the ratio of fiber length to diameter) of about 1:1 to about 50:1, about 10:1 to about 40:1, about 5:1 to about 10:1, or about 2:1 to about 5:1. Bone chips may have a size, for example, of about 1 mm to about 10 mm, about 1 mm to about 2 mm, about 1 mm to about 4 mm, about 1 mm to about 6 mm, about 2 mm to about 4 mm, about 2 mm to about 6 mm, about 4 mm to about 6 mm, about 6 mm to about 8 mm, or about 8 mm to about 10 mm across the largest dimension. Bone particles or particulates may range in size, for example, from about 0.01 to about 2 mm, about 0.1 mm to about 1.0 mm, about 100 to about 500 microns, or about 100 to about 400 microns. It will be appreciated that some variation in dimension is possible in the production of the demineralized bone materials.

In some embodiments, the bone used to manufacture the demineralized bone matrix can be cortical, cancellous, cortico-cancellous of autogenous, allogeneic, xenogeneic or transgenic in origin. Thus, the fibers, chips, or particulates, for example, can include cortical, cancellous, or cortico-cancellous bone. Preferably, the demineralized bone is in the form of fibers derived from cortical bone, powder derived from cortical bone, and/or chips derived from cortico-cancellous bone.

To prepare bone matrix, the bone material is typically treated to clean, defat, sterilize, virally inactivate, disinfect, demineralize, dehydrate, and/or dry the bone matrix. Methods for preparing DBM are known to persons of ordinary skill in the art and include, but are not limited to, shaving bone into thin shavings or fibers, milling, grinding, or crushing bone into chips or particles, or the like. Before or after processing the bone, the bone material is subjected to demineralization so as to reduce inorganic content to low levels. For example, demineralized bone can be produced by acid extraction, thermal freezing, irradiation, or physical extraction of inorganic minerals from human or animal bone. In an acid extraction, inorganic acids such as hydrochloric acid or phosphoric acid, or organic acids such as formic acid, acetic acid, peracetic acid, citric acid, propionic acid, etc. may be used. As would be recognized by one of ordinary skill in the art, the amount and depth of demineralization into the bone surface can be controlled by adjusting the treatment time, temperature of the demineralizing solution, concentration of the demineralizing solution, agitation intensity during treatment, and the like.

The term "demineralized" refers to bone or bone material containing less than its original mineral content (e.g., calcium content) and may encompass "substantially demineralized," "partially demineralized," and "completely demineralized" bone material. For example, the demineralized bone may include less than 10%, less than 9%, less than 8%, less than 7%, less than 6%, less than 5%, less than 4%, less than 3%, less than 2%, or less than 1% of the original mineral content (e.g., calcium content) of the bone.

If present, the demineralized bone matrix may be included in the composition, for example, in amounts ranging from about 1-60% (w/w), about 10-60% (w/w), about 15-60% (w/w), about 20-60% (w/w), about 30-60% (w/w), about 10-50% (w/w), about 20-50% (w/w), about 30-50% (w/w), about 10-40% (w/w), about 20-40% (w/w), about 30-40% (w/w), about 10-35% (w/w), about 20-35% (w/w), about 30-35% (w/w), about 10-30% (w/w), about 20-30% (w/w), or about 20-25%. In particular, when present, the composition may include demineralize bone powder, demineralized bone chips, or a combination thereof. For example, the demineralized bone powder may be present in amounts ranging from about 15-60% (w/w), about 15-50% (w/w), about 15-40% (w/w), about 15-30% (w/w), about 15-20% (w/w), about 20-60% (w/w), about 20-50% (w/w), about 20-40% (w/w), about 20-30% (w/w) about 30-60% (w/w), about 30-50% (w/w), or about 30-40% (w/w). For example, demineralized bone chips may be present in amounts ranging from about 1-20% (w/w), about 5-20% (w/w), about 10-20% (w/w), about 15-20% (w/w), 1-15% (w/w), about 5-15% (w/w), about 10-15% (w/w), 1-10% (w/w), about 5-10% (w/w), or 1-5% (w/w).

According to certain embodiments, the compositions may include a ceramic component. For example, the ceramic may include ceramic mineral or inorganic filler useful for promoting bone formation. The ceramic component may include, but is not limited to, synthetic and naturally occurring inorganic fillers such as alpha-tricalcium phosphate, beta-tricalcium phosphate, tetra-tricalcium phosphate, dicalcium phosphate, calcium carbonate, barium carbonate, calcium sulfate, barium sulfate, hydroxyapatite (HA), biphasic calcium phosphate (e.g., composite between HA and β-TOP), bioactive glass, and combinations and mixtures thereof. Tricalcium phosphate and bioactive glass share similar surface properties and show enhanced osteoconductivity in in vivo settings. Tricalcium phosphate has a similar composition to hydroxyapatite, but resorbs faster due to a lower calcium to phosphate (Ca/P) ratio. For example, hydroxyapatite has a Ca/P ratio of about 1.67 whereas tricalcium phosphate has a Ca/P ratio of about 1.5.

If present, one or more ceramics may be included in the composition depending on the type or types of ceramic present, for example, in amounts ranging from about 10-40% (w/w), about 10-30% (w/w), about 10-20% (w/w), about 25-35% (w/w), about 20-40% (w/w), about 20-30% (w/w), about 15-40% (w/w), about 15-30% (w/w), or about 15-20% (w/w), about 40-70% (w/w), about 40-80% (w/w), about 50-70% (w/w), about 50-80% (w/w), about 60-70% (w/w), about 60-80% (w/w), or about 65-70% (w/w), 50-95% (w/w), about 60-95% (w/w), about 70-95% (w/w), about 75-95% (w/w), about 50-90% (w/w), about 60-90% (w/w), about 70-90% (w/w), about 75-90% (w/w), about 80-90% (w/w), or about 85-90% (w/w).

In certain embodiments, the ceramic comprises beta-tricalcium phosphate (TCP). The calcium phosphate may be configured to facilitate regrowth of bone at the target repair site. In some embodiments, the calcium phosphate of the bone graft composition is an osteoinductive agent. The calcium phosphate is configured to be disposed on, embedded in, or otherwise mixed within the biomaterial composition. The calcium phosphate can be in any suitable form. For example, the calcium phosphate can be in particulate or granular form. The calcium phosphate may have a particle size ranging from about 1 to 500 μm, about 25 to about 450 μm, about 50 to about 400 μm, about 75 to about 300 μm, or about 100 to about 250 μm. The calcium phosphate may be porous or non-porous. Preferably, the calcium phosphate is a non-porous tricalcium phosphate.

If present, tricalcium phosphate may be included in the composition, for example, in amounts ranging from about 40-70% (w/w), about 40-80% (w/w), about 50-70% (w/w), about 50-80% (w/w), about 60-70% (w/w), about 60-80% (w/w), or about 65-70% (w/w).

The ceramic may also comprise a bioactive glass. The bioactive glass may also be configured to facilitate the regrowth of bone at the target repair site. In some embodiments, the bioactive glass can be an osteoconductive agent. Bioactive glass possesses osteostimulative properties, which may be useful in the regeneration of hard tissues. The bioactive glass can be disposed on, embedded within, and or mixed within the biomaterial composition. The bioactive glass can be any alkali-containing ceramic, glass, glass-ceramic, or crystalline material that facilitates bone formation after contact with a biological environment. Suitable bioactive glasses include sol gel derived bioactive glass, melt derived bioactive glass, silica based bioactive glass, silica free bioactive glass such as borate based bioactive glass and phosphate based bioactive glass, crystallized bioactive glass (either partially or wholly), and bioactive glass containing trace elements or metals such as copper, zinc, strontium, magnesium, zinc, fluoride, mineralogical calcium sources, and the like.

Exemplary bioactive glass can include bioglass 45S5 (46.1 mol % $SiO_2$, 26.9 mol % CaO, 24.4 mol % $Na_2O$ and 2.5 mol % $P_2O_5$), 58S (60 mol % $SiO_2$, 36 mol % CaO and 4 mol % $P_2O_5$), 70S30C (70 mol % $SiO_2$, 30 mol % CaO), or a combination of the foregoing bioglass. The bioactive glass may take the form of fibers, granules, particles, or a combination thereof. The bioactive glass may be irregular in shape, for example. The bioactive glass may have a uni-modal or bimodal particle size distribution. The bioactive glass may have a particle size, for example, ranging from about 1 to 1000 μm, about 50 to 750 μm, or about 75 to 500 μm. Particle size and distribution may be determined by routine techniques known in the art including sieve analysis or BET (Brunauer, Emmett and Teller) testing, for example.

If present, bioactive glass may be included in the composition, for example, in amounts ranging from about 10-40% (w/w), about 10-30% (w/w), about 10-20% (w/w), about 25-35% (w/w), about 20-40% (w/w), about 20-30% (w/w), about 15-40% (w/w), about 15-30% (w/w), or about 15-20% (w/w).

According to certain embodiments, the compositions may include collagen. The collagen may have osteoconductive properties, for example, to function as a scaffold at the target repair site. The collagen can be or include soluble collagen, insoluble collagen, or a combination thereof. The collagen can be or include type I collagen, type II collagen, type III collagen, type VII collagen, another suitable type of collagen, or a combination thereof. The collagen can be derived from human, equine, bovine, porcine, murine, synthetic, or from another suitable source. In one embodiment, the collagen is of mammalian origin, preferably human. The collagen may be in particulate, gel, or another suitable form. The collagen may be porous or non-porous.

If present, collagen may be included in the composition, for example, in amounts ranging from about 1-20% (w/w), about 1-15% (w/w), about 1-10% (w/w), about 1-5% (w/w), about 5-20% (w/w), about 5-15% (w/w), about 5-10% (w/w), about 8-20% (w/w), about 8-15% (w/w), or about 8-10% (w/w).

In addition to or in place of collagen, one or more carrier, scaffold materials, or processing additives may be used in the biomaterial composition. The carrier may affect the overall handling of the material and can influence the safety, efficacy, and functionality of the material (e.g., osteoinductivity). Preferably, the carrier is inert or enhances osteogenic, osteoinductive, osteoconductive, and/or osteostimulative properties of the composition. Suitable carriers, scaffolds, or additives may include, but are not limited to, phospholipids, carboxylmethylcellulose (CMC), glycerin, glycerol, polyethylene glycol (PEG), hydrogels, poloxamers, polylactic acid (PLA), polylactic-co-glycolic acid (PLGA), other copolymers of the same family, and combinations thereof.

By way of example, the carrier may include a hydrogel, including a reverse phase hydrogel or temperature sensitive hydrogel, such as a poloxamer (e.g., a PEO-PPO-PEO triblock copolymer). In particular, the poloxamer may include poloxamer 407, poloxamer P188, poloxamer P338, or the like. The poloxamer may also be chemically modified, for example, where one or more of the terminal hydroxyl groups are replaced with methoxy groups. Other suitable materials may include hyaluronic acid (HA), sodium alginate, saline or bone marrow aspirate, for instance. The carrier, scaffold materials, or processing additives may be either water-based or non-water based.

If present, one or more carriers may be included in the composition, depending on the type or types of carrier in amounts ranging from, for example, about 1-20% (w/w), about 1-15% (w/w), about 1-10% (w/w), about 1-5% (w/w), about 5-20% (w/w), about 5-15% (w/w), about 5-10% (w/w), about 8-20% (w/w), about 8-15% (w/w), or about 8-10% (w/w), about 10-40% (w/w), about 10-30% (w/w), about 10-20% (w/w), about 25-35% (w/w), about 20-80% (w/w), about 20-70% (w/w), about 20-60% (w/w), about 20-50% (w/w), about 20-40% (w/w), about 20-30% (w/w), about 15-40% (w/w), about 15-30% (w/w), or about 15-20% (w/w), about 40-70% (w/w), about 40-80% (w/w), about 50-70% (w/w), about 50-80% (w/w), about 60-70% (w/w), about 60-80% (w/w), or about 65-70% (w/w), 50-95% (w/w), about 60-95% (w/w), about 70-95% (w/w), about 75-95% (w/w), about 50-90% (w/w), about 60-90% (w/w), about 70-90% (w/w), about 75-90% (w/w), about 80-90% (w/w), or about 85-90% (w/w).

In the case of a hydrogel, such as a poloxamer, hyaluronic acid or alginate, the materials may be swellable in volume. For example, the carrier (e.g., HA) may be mixed with water, a buffer, or an acid, such as hydrochloric acid, nitric acid, sulfuric acid, or the like, which causes the carrier to swell in volume. In an exemplary embodiment, hyaluronic acid is swellable in volume when immersed in hydrochloric acid. As will be recognized by one of ordinary skill in the art, swelling of the hydrogel may be influenced by a number of factors, such as temperature, surface area, molecular weight, degree of crosslinking, pH, or the like. By way of example, the carrier may be swellable at a reduced temperature, for example, in the range of about 1-15° C., about 1-10° C., about 1-6° C., about 2-4° C., about 2-5° C., about 2-6° C., about 3-6° C., or about 3-5° C.

If present, hyaluronic acid may be included in the composition, for example, in amounts ranging from about 0.1-5% (w/w), about 0.1-2% (w/w), about 1-5% (w/w), about 1-4% (w/w), about 1-3% (w/w), about 1-2% (w/w), or about 2% (w/w).

If present, poloxamer may be included in the composition, for example, as a hydrogel comprised of a mixture of poloxamer and water in amounts ranging from about 10-50% poloxamer, about 10-40% poloxamer, about 10-30% poloxamer, about 20-50% poloxamer, about 20-40% poloxamer, about 20-30% poloxamer, about 30-50% poloxamer, about 30-40% poloxamer with the remainder being water. The hydrogel mixture may be present in the final composition, for example, in amounts ranging from about 50-90% (w/w), about 50-80% (w/w), about 50-75% (w/w), about 60-90% (w/w), about 60-80% (w/w), about 60-75% (w/w), about 65-80% (w/w), about 65-75% (w/w), about 60-80% (w/w), or about 60-75% (w/w).

Additionally, biological agents may be added to the biomaterial or implant. These biological agents may comprise bone morphogenic protein (BMP), a peptide, a bone growth factor such as platelet derived growth factor (PDGF), vascular endothelial growth factor (VEGF), insulin derived growth factor (IDGF), a keratinocyte derived growth factor (KDGF), or a fibroblast derived growth factor (FDGF), stem cells, bone marrow, and platelet rich plasma (PRP), to name a few. If desired, one or more active pharmaceutical ingredients or medicaments may be incorporated into the biomaterial or implant as well. Biological agents may be added in any suitable pharmaceutically acceptable and effective amounts known in the art.

According to one embodiment, the composition includes a scaffold containing TCP and bioactive glass to aid in bone regeneration. In particular, a bioactive ceramic scaffold may be produced by combining tricalcium phosphate and bioactive glass. In addition, the bioactive scaffold containing tricalcium phosphate and bioactive glass may optionally be mixed with one or more of bovine type I collagen, hyaluronic acid, glycerol, and/or polyethylene glycol to facilitate handling properties. These biomaterials may possess sufficient osteoconductivity, porosity, mechanical strength, and degradation times for the intended application.

According to a particular embodiment, the composition includes a bioactive scaffold including about 50-65% (w/w) tricalcium phosphate and about 20-35% (w/w) bioactive glass. In addition, the bioactive scaffold may include about 4-12% (w/w) collagen and about 1-3% (w/w) hyaluronic acid. According to another embodiment, the composition includes a bioactive scaffold including about 60-70% (w/w)

tricalcium phosphate and about 15-30% (w/w) bioactive glass. In addition, the bioactive scaffold may include about 8-15% (w/w) collagen and about 0.1-2% (w/w) hyaluronic acid.

According to another embodiment, the composition includes a scaffold containing demineralized cortical fibers, demineralized bone powder, TCP, and bioactive glass to aid in bone regeneration. In addition, the bioactive scaffold may optionally be mixed with one or more of hyaluronic acid, poloxamer, glycerol, and/or polyethylene glycol to facilitate handling.

According to yet another embodiment, the composition includes demineralized bone powder and a hydrogel. For example, the composition may include demineralized bone powder, poloxamer, water, and optionally demineralized bone chips. In particular, the composition may include about 15-60% (w/w) of demineralized bone powder and about 40-85% (w/w) carrier including about 15-40% (w/w) poloxamer with the remainder water. According to another embodiment, the composition includes about 2040% (w/w) of demineralized bone powder, up to 20% (w/w) demineralized bone chips, and about 60-80% (w/w) carrier including about 30-40% (w/w) poloxamer with the remainder water.

The biomaterial composition may be obtained using any suitable procedures and techniques known in the art. For example, components of the composition described herein may be mixed together to form the resulting composition. The components may be combined under agitation, for example, at room temperature (e.g., about 20 and 26° C.), an elevated or reduced temperature, or any other suitable temperature and conditions known in the art.

The biomaterial composition may be added to a mold to form a molded biomaterial composition. The form or mold may be of any suitable size and shape to obtain the desired shaped implant. In particular, the mold may be provided under a given pressure and temperature necessary to form a compressed implant. Preferably, the mold is provided under an elevated pressure (i.e., greater than atmospheric) sufficient to compress the biomaterial into a solid form. The biomaterial or resulting implant may be formed, for example, in the shape of putty, gel, paste, strip, sheet, morsels, sponge, crunch, extrudable or flowable material (e.g., from a syringe), or the like. In addition, a pattern or design may be cut into or from the molded implant to form other desired shapes.

The resulting material may be solid, layered, non-porous, porous, sponge-like, or of any other suitable configuration. For example, it may be desirable that the resulting biomaterial or implant is substantially non-porous. In an alternative embodiment, the resulting biomaterial or implant may be partially or completely porous (e.g., having a porosity). For example, the average pore size may range from about 1-1000 microns, about 50-750 microns, or about 200-500 microns. Pore size may be determined by routine techniques known in the art including measurements via $N_2$ adsorption, BET (Brunauer, Emmett and Teller) testing, for example.

The compositions may be sterilized, for example, by subjecting the material to chemical and/or radiation sterilization. For example, chemical sterilization may include exposure to a chemical sterilizing agent, such as ethylene oxide, nitrogen dioxide, ozone, or the like. Radiation sterilization may include exposing the material to a sterilizing source such as gamma, x-ray, and/or electron irradiation. The composition may be dehydrated or dried, for example, by air or by freeze-drying. Freeze-drying may include freezing the material (e.g., in liquid nitrogen) and reducing the surrounding pressure to allow the frozen water in the material to sublimate directly from the solid phase to the gas phase. In addition, the composition may be partially of fully crosslinked. For example, crosslinking may occur by exposing the material to a chemical crosslinking agent including mono aldehydes such as formaldehyde, acetaldehyde, or glutaraldehyde. In addition or in the alternative, crosslinking may occur by exposing the material to a crosslinking source, such as gamma, ultraviolet, or thermal sources.

In addition, the biomaterial may be formed into a specific size and shape for a desired application. For example, the implant may have a footprint suitable for cervical, thoracic, or lumbar applications. The implant may be shaped, for example, in the form of a strip, ring, cylinder, plug, or the like. The implant may be provided with one or more openings or windows suitable to be filled with the biomaterials described herein or other graft materials known in the art. The implant may be used alone or in combination with a cage, frame, allograft, graft material, or other biomaterials known in the art. The implants may be suitable for an anterior, posterior, lateral, oblique, anterolateral, transforaminal approach, or other suitable approach known in the art.

The biomaterial and implant formed therefrom is intended to be applied at a bone repair site, e.g., one resulting from injury or defect. The implant can be utilized in a wide variety of orthopedic, periodontal, neurosurgical, oral and maxillofacial surgical procedures. In particular, the biomaterials may be suitable for repairs of the vertebral column including spinal fusion and internal fixation; tumor surgery, e.g., deficit filling; discectomy; laminectomy; scoliosis, lordosis and kyphosis treatments. Possible clinical applications may include e.g., the treatment of spinal disc degeneration or disease, traumatic, pathologic, or stress fractures, congenital defects or fractures, or operative defects in any bone or between bones of the body.

The compositions and implants may be configured for use at various target repair sites within a body of a patient to facilitate bone growth therein. In some embodiments, the composition is configured for use at a target repair site in the patient's spine. For example, the composition can facilitate growth of bone between the body of a first vertebra and the body of a second vertebra to achieve interbody fusion of the two vertebrae. In a spinal fusion procedure, the composition may be used in conjunction with one or more mechanical supports (e.g., a cage or frame, spacer, plate, a plurality of screws and/or rods, or the like). Although the spine is described, the composition can be configured to be implanted into or at a target repair site in or at a different bone or bony structure of the patient's body.

The term "treating" and the phrases "treatment of a disease" and "treatment of a condition" refer to executing a protocol that may include the use of the compositions, devices and methods herein and/or administering one or more biomaterials to a patient (human, normal or otherwise, or other mammal), in an effort to alleviate signs or symptoms of the disease or condition. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms and does not require a cure to the ailment.

Further example embodiments are directed to kits that include components for making the present biomaterials and implants, including for example, carriers or scaffolds, cages (e.g., titanium and/or polyether ether ketone (PEEK) spacers), allograft spacers, demineralized bone materials, cell culture media, phosphate buffered saline (PBS), a tissue culture substrate such as a flask, trypsin, or mixtures, bone graft harvesting tools, bone marrow aspirate retrieval tools, or the like. Additional components, instructions and/or apparatus' may also be included.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLE

In this example, a bioactive ceramic scaffold is made using tricalcium phosphate, a bioactive glass, and collagen. Putty and strip formulations were developed as provided in the table below:

|  | Putty | Strip |
| --- | --- | --- |
| TCP | 60-70% (w/w) | 55-65% (w/w) |
| Bioactive glass | 15-20% (w/w) | 10-20% (w/w) |
| Collagen | 6-10% (w/w) | 12-15% (w/w) |
| Hyaluronic Acid | up to 2% (w/w) | less than 1% (w/w) |

First, the collagen and hyaluronic acid were mixed in hydrochloric acid and allowed to swell at 4° C. for up to 24 hours. At the end of the swelling, the mixture was combined with TCP and bioactive glass and mixed thoroughly. In the case of the strips, the mixture was poured into molds, frozen, and freeze-dried. The freeze-dried strips were crosslinked using a formaldehyde crosslinking agent and residual formaldehyde was removed with rinsing in deionized water. The final products were sterilized using ethylene oxide. The putty was moldable and the strips were flexible. The putty and strips exhibited osteoconductive and osteostimulative properties, which aids in bone regeneration.

Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. A method of making an implantable biomaterial for aiding bone regeneration, the method comprising:
    mixing a hydrogel carrier with a ceramic composition including bioactive glass and calcium phosphate to form a biomaterial composition, wherein the biomaterial composition includes about 5-20% (w/w) of the hydrogel carrier, about 15-20% (w/w) of the bioactive glass, and about 60-70% (w/w) of the calcium phosphate, wherein the hydrogel carrier includes hyaluronic acid mixed in hydrochloric acid;
    adding the biomaterial composition to a mold to form a molded biomaterial composition;
    freeze-drying the molded biomaterial composition to form a freeze-dried composition; and
    crosslinking the freeze-dried composition to form a crosslinked composition.

2. The method of claim 1 further comprising adding demineralized bone matrix to the biomaterial composition.

3. The method of claim 2, wherein the demineralized bone matrix is in the form of demineralized cortical fibers.

4. The method of claim 2, wherein the demineralized bone matrix is in the form of demineralized cortical bone chips.

5. The method of claim 1, wherein the calcium phosphate is beta-tricalcium phosphate.

6. The method of claim 1, wherein the hydrogel carrier includes poloxamer.

7. The method of claim 1, wherein the bioactive glass has a particle size ranging from about 1 to 1000 μm.

8. The method of claim 1 further comprising, before mixing the hydrogel carrier with the ceramic composition, allowing the hydrogel carrier to swell in volume.

9. The method of claim 1 further comprising crosslinking the freeze dried composition with a chemical crosslinking agent.

10. The method of claim 9, wherein the chemical crosslinking agent is formaldehyde.

11. The method of claim 1 further comprising sterilizing the crosslinked composition with ethylene oxide.

12. The method of claim 1 further comprising sterilizing the crosslinked composition with gamma radiation.

13. The method of claim 1, wherein the biomaterial composition is in the form of a strip.

14. The method of claim 3, wherein the demineralized cortical fibers have an average fiber length of about 250 μm to 2 mm.

15. The method of claim 14, wherein the demineralized cortical fibers have an aspect ratio of fiber length to diameter of about 10:1 to 40:1.

16. The method of claim 1, wherein the calcium phosphate has a particle size ranging from about 1 to 500 μm.

17. The method of claim 8, wherein the hydrogel carrier is swellable in volume at a reduced temperature of about 1-15° C.

18. The method of claim 1, wherein the biomaterial composition includes a biological agent including bone morphogenic protein (BMP), stem cells, or a bone growth factor.

* * * * *